US00PP08812P

United States Patent [19]

Probasco

[11] Patent Number: Plant 8,812

[45] Date of Patent: Jun. 28, 1994

[54] HOP PLANT NAMED H87311-3

[75] Inventor: Gene Probasco, Yakima, Wash.

[73] Assignee: John I. Haas, Inc., Yakima, Wash.

[21] Appl. No.: 992,481

[22] Filed: Dec. 17, 1992

[51] Int. Cl.[5] ..... A01H 5/00

[52] U.S. Cl. ..... Plt./100

[58] Field of Search ..... Plt. 100

[56] References Cited

PUBLICATIONS

John I. Haas Co., Inc. "Farming" 1987 30 pages.

John I. Haas Co., Inc. "U.S. Hop Industry Information Manual" 1985 13 pages.

John I. Haas Co., Inc., "Hop Research & Development" 1989 9 pages.

John I. Haas Co., Inc. "Hop Pellets—Regular and Concentrated/Technical Data" 1985 9 pages.

John I. Haas Co., Inc. "Non-isomerized Hop Extract—Technical Data" 1985 13 pages.

John I. Haas Co., Inc. "Isomerized Hop Extract—Technical Data" 1985 9 pages.

John I. Haas Co., Inc. "Hop Varieties—U.S. Grown" 8 pages.

*Primary Examiner*—James R. Feyrer

*Attorney, Agent, or Firm*—Stratton Ballew Richardson

[57] ABSTRACT

A new variety of hop plant (H87311-3) originating as the result of a controlled cross pollination between an unpatented John I. Haas, Inc. female hop plant No. 832-17 with an unpatented John I. Haas, Inc. male hop plant No. 833-53M, and unique particularly for its cones' unusually high percentage of alpha acids when compared to its female grandparent variety Galena (unpatented) and otherwise as herein described.

2 Drawing Sheets

BACKGROUND AND SUMMARY OF INVENTION

Hops are grown commercially for use in flavoring beers, stouts and ales. Lupulin glands inside female hop cones provide the resins and essential oils which are the primary components of the hop flavor each variety imparts to beers, stouts, and ales. New hop varieties are evaluated for their growing characteristics, per acre hop cone yield (dried to approximately 8% moisture), the chemical composition of the resins and essential oils contained within the hop cone's lupulin glands, and the unique flavor each variety imparts to beers, stouts and ales. Only female hop plants produce cones containing lupulin glands, and thus only female hops have any commercial value. Male hop plants have no commercial value other than for use in breeding programs to create new varieties.

This invention relates to a new and distinct variety of hop and more particularly to an asexually reproduced hop variety selected from among hop plants resulting from a controlled cross pollination between an unpatented John I. Haas, Inc. (Haas) female hop No. 832-17 with unpatented Haas male hop NO. 833-53M.

Haas female hop No. 832-17 originated from a controlled cross pollination in 1982 between unpatented Galena female hop and unpatented male hop USDA Accession No. 63015M. Haas male hop No. 833-53M originated from a controlled cross pollination in 1982 between unpatented female hop USDA Accession No. 21055 and unpatented male hop USDA Accession No. 63015M.

The controlled cross pollination program resulting in the creation of the new hop variety, hereafter called "H87311-3", was performed in 1986 by Mr. Gene Probasco, a botanist employed by John I. Haas, Inc., in a Haas greenhouse located at 1112 North 16th Avenue, Yakima, Wash. 98902. Mr. Probasco discovered the H87311-3 variety in 1988, among the hop plants which were produced from the seeds resulting from the above described controlled cross pollination progrm.

The seeds from the cross between Haas female hop No. 832-17 and Haas male hop No. 833-53M were planted in a Haas greenhouse in 1987. The most vigorous plants resulting from the cross were selected and planted in a Haas hop field located at Wada Farm, Yakima Golding Farms, Toppenish, Wash. This planting did not produce a crop during the planting year.

In 1988, as a result of chemical analysis and field observations of the hop plants resulting from the Haas female 832-17×Haas male 833-53M cross, Mr. Probasco was attracted to the H87311-3 hop plant for its unusually high percentage of alpha acids coupled with its reasonable projected per acre cone yield. The per acre cone yield projections were based upon the cone production of the single H87311-3 hop plant observed in 1988. The plant of this application has been repeatedly asexually reproduced by rooting cuttings at the address identified above. The clones of this plant have been observed to be identical to the original selection in every distinguishing characteristic and establish that the plant is genetically stable through successive generations by asexual propagation.

In 1989, second (2nd) generation rootstock from the H8731 1-3 variety was planted in a one acre test plot located at Wada Farm. This greenhouse produced planting did not produce a crop during the planting year.

However, in 1990, chemical analysis and field observations of the first harvestable crop of the second (2nd) generation plants in the one-acre test plot provided additional information supporting the per acre cone yield projections made from the original H87311-3 plant selected in 1988; confirmed the unusually high alpha acids percentage characteristics of the new variety; and initiated the accumulation of historical agronomic data on the new variety. It is important to note that first year per acre cone yields in Washington state typically are lower than normal per acre yields for Washington state hop fields in subsequent years. Consequently, the per acre cone yield observations made from this first year one acre test plot were used to merely project anticipated normal yields for the new variety.

Also, in 1990, John I. Haas, Inc., performed the first year trials of hexane extraction of the alpha acids on bales of the H87311-3 hop variety from the first crop produced from the one acre test plot. These initial extraction trials were successful because Haas was able to extract a minimum of 93% of the alpha acids present in the H87311-3 hop cones. John I. Haas, Inc. requires that a minimum of 93% of alpha acids be extractable from a new hop variety in order for the new variety to be considered potentially commercially viable.

In 1991, second (2nd) and third (3rd) generation rootstock from the H87311-3 variety was planted in a larger test plot of approximately 10 acres (large acreage test plot) at one of John I. Haas, Inc.'s hop farms located at Toppenish, Wash. This planting did not yield a crop in 1991.

However, in 1991, the one acre test plot of second (2nd) generation plants at Wada Farm produced a second crop of hop cones. The second year per acre cone production was two thousand three hundred and ninety eight (2398) pounds per acre. This is well within the range of per acre cone production for a commercially viable hop variety. The analytical data from chemical analysis of multiple random samples from bales of cones harvested from the one acre test plot showed an average alpha acids percentage of 18.2% (ASBC spectrophotometric method). This is an unusually high alpha acids percentage, and is the primary novel characteristic of this new variety.

In 1991, John I. Haas, Inc., also performed the second year trials of hexane extraction of the alpha acids on bales of the H87311-3 hop variety from the second crop produced from the one acre test plot. These initial extraction trials confirmed that Haas was again able to extract a minimum of 93% of the alpha acids present in the H87311-3 hop cones.

In 1992, no new rootstock was planted. Instead, the second (2nd) generation rootstock in the one acre test plot at Wada Farm was subjected to a third year of field observation and chemical analysis. In 1992, the third year per acre cone production was two thousand and twenty (2020) pounds per acre. This is still well within the range of per acre cone production for a commercially viable hop variety, but was on the low side due to slightly adverse seasonal weather conditions during the 1992 growing season. The analytical data from chemical analysis of multiple random samples from bales of cones harvested from one acre test plot showed an average alpha acids percentage of 17.8%. The third year hexane extraction trials confirmed again that Haas was able to consistently extract a minimum of 93% of the alpha acids present in second (2nd) generation H87311-3 hop cones.

Also, in 1992, the large acreage test plot of second (2nd) and third (3rd) generation plants produced its first crop of hop cones. The analytical data from chemical analysis of multiple random samples from bales of cones harvested from the large acreage test plot in 1992 showed an average alpha acids percentage of 18.2%. Field observations showed hop cone yields of one thousand six hundred and fifty (1650) pounds per acre. Again it is important to note that first year per acre cone yields in Washington state typically are lower than normal per acre yields for Washington state hop fields in subsequent years. This first year yield for hop cones in a large acreage test plot in Washington state were well within the accepable range for a commercially viable variety.

All of the testing and evaluation of the H87311-3 variety's growing characteristics, per acre hop cone yield, analytical data and alpha acids extraction tests were carried out on hop farms, laboratory facilities, and industrial extraction facilities which are wholly owned and controlled by John I. Haas, Inc.

No brewing trials for any beers, stouts or ales had been conducted on this new variety as of the end of the 1992 growing season.

Based upon the field observations performed, and chemical analytical data collected, during this testing and evaluation program from 1988 through 1992, it appears that second (2nd) and third (3rd) generation H87311-3 hop plants demonstrate genetic stability with respect to the new variety's novel characteristic of unusually high alpha acids yields. Also, the new H87311-3 variety demonstrates genetic stability with respect to the production of commercially viable per acre hop cone yields.

This new hop variety has been carefully compared to its female parent, the unpatented Haas female hop No. 832-17, and to its unpatented grandmother variety Galena. (Please note that the hop industry does not make or rely upon any comparisons between new varieties and their male parents or male grandparents, because male hops have no commercial value.). The primary difference between the new H87311-3 variety and its female parent and grandparent varieties is the unusually high alpha acids percentages in bales of harvested hop cones.

THE DRAWINGS

The accompanying photographs illustrate the cones of the new H87311-3 hop variety.:

The top photograph of Sheet 1 depicts mature cones, late season foliage and stems of the plant of this invention.

The bottom photograph on Sheet 1 depicts the lateral stems of the plant and the cone and leaf arrangement.

The top photograph on Sheet 2 shows a lateral with cones and leaves.

The bottom photograph on Sheet 2 shows the new variety growing on a typical hop trellis.

DESCRIPTION OF THE VARIETY

This description contains information about all botanical and analytical chemical characteristics upon which the hop industry relies in identifying and distinguishing specific hop varieties. The analytical data used to describe this new variety is subject to some variation between different samples of this new variety, due to the maturity of the hop cones sampled, climatic and growing conditions, geography, and other varieties. For this reason the analytical values used to describe this new variety are expressed in terms of ranges or averages of values rather than absolute or fixed values.

General Descriptive Information

I. Introduction

The hop plant, *Humulus lupulus,* is a perennial plant which produces annual climbing bines and a perennial crown. The bine, or vine as it is often called, can grow up to 25 feet in a single growing season. These bines climb in a clockwise direction without the aid of tendrils, but rather with the aid of hooked hairs known as tricomes. The bine of a mature hop may be one half to three quarters of an inch thick at the six foot height. In the spring the buds which have developed on the crown send out numerous shoots. Laterals grow from the axillary buds at each node along the main bine. The inflorescences develop from the axils of the laterals and each inflorescence becomes a single hop cone at maturity.

II. Roots

The hop crown will become woody with age, having heavy, rough bark after the first year. Much of the hop crown consists of branched stem tissue which lies buried at a shallow depth below the soil surface. This stem tissue, or rhizome, produces buds which in the spring develop into a mass of shoots. The crown also produces two types of roots; horizontal and vertical. The horizontal roots are fibrous, absorptive roots used for water uptake. The vertical roots, which develop from the horizontal roots, are thick and fleshy and serve as a carbohydrate storage organ.

III. Stems

The stems grow from the crown in early spring and twine around suitable support. Shoots of H87311-3 emerge from winter dormancy about the same time as the commercial variety Galena. They are hexagonal in shape with the corners of the hexagon often protruding. On all sides of the stem are hairs, consisting mostly of silicates, and as these harden they become one or two sided hooks. Generally, the size of the stem at the six foot level is between ⅜" to ½" in diameter. The main stem color is green and the stripe along the edges is also green.

The hop bine can grow to a height of 20–24 feet. The trellis system on which the hop plant grows is 18 feet high. Therefore, the bine will grow to a height of 18 feet and then will grow laterally along the trellis. The laterals which develop farther up the bine are slightly longer, and can develop secondary branching. As cones develop the sidearms begin to recline (descend downward at a 106°–135° angle from central axis), therefore forming a head-shaped growth form near the trellis. This grown habit is described as "capitate," meaning that the majority of hop production is produced from lateral growth along the top wire of the trellising system. The remainder of the production is on the rest of the bine.

The first "training" for the variety H87311-3 is ideally during mid-May. "Training" is a term used by growers to describe placement of the vines on a support, which is attached at one end to the 18 foot high trellis, and the other end secured into the soil. During training, the vines are placed on the support in a clockwise manner, which is the natural helical growth pattern of all hop varieties.

IV. Leaves

Leaves of H87311-3 are borne in pairs at each node on the bine. On the stem of the plant the majority of the leaves are opposite in arrangement. Located at the base are stipules which are interpetiolar in arrangement. Bine leaves are cordate in shape with 3–5 lobes and palmate venation. The sinus cleft are deeply cut with leaf margins being smooth. The remainder of the leaf margins are serrate to dentate. The color is a very dark green on the upper leaf surface and lighter green on the lower surface of the leaf. Stiff fine hairs on the upper surface of the leaf give a dull appearance and rough texture. The lower surface bears many disc-shaped yellowish resin glands.

The leaves are petiolate and said to be slightly channelled, therefore having a flat surface on the upper side of the petiole. The leaf petiole extends from the main vine in a reflexed position.

V. Laterals

The laterals, or sidearms as they are often called, originate from buds in the axils of leaves or stems. The sidearm position is "calous," which means to grow more or less evenly spaced along the main bine.

VI. Cones

The inflorescence of H87311-3 begin to appear in late June and mature during the first week of September. As they mature, they form a conelike structure or strobile, referred to as a "cone." These inflorescences develop on a cranked axis and the cones form in pairs or clusters. The cones develop on the laterals from the top of the plant to approximately 40 inches above the ground. The cone consists of a central rachis or strig which bears numerous bracts and bracteoles. At the base of each bracteole is an ovary. Pollination of the ovary results in the lengthening and thickening of the central strig. The plant variety H87311-3 is not fertilized, and therefore unseeded because of the brewers do not want seeded cones.

The aroma of the cone is regarded by the inventor as pleasant. However, please note that hop aroma is not defined nor measurable and therefore highly subjective.

The hop cone of H87311-3 is ovoid in shape and is of medium tight compactness. The bract tip shape is attenuate to acute, while the bracteole is narrowly rounded. The tip of the cone is pointed. The central rachis or strig is considered to be thick as compared to the variety Cluster. The cone and more specifically the bracteoles, contain numerous lupulin glands which contain resins which are the commercial value of the crop. The lupulin glands are cup shaped and white to creamy yellow in color. As the hop cone matures, the lupulin glands fill and form a globular shape and are golden yellow in color. The most important component of these resins is the alpha acid which gives beer its bitterness. Other components of the lupulin glands also contribute to the flavor of the beer.

The cone numbers and cone size are direct factors in determining the yield of the variety. Climatic fluctuations, as well as cultural practices, soil type and fertility all have dramatic effects on yield. Cone uniformity with regard to size and level of maturity varies with the growing season. Cone shape is fairly uniform for the H87311-3 variety.

The hop cones of the H87311-3 variety are well adapted to mechanical harvest because of their compactness and ovoid shape. The cones do not shatter during harvest.

VII. Growth Characteristics

Growth of the annual stem is extremely rapid during a relatively short thirty day period during which the bine will grow approximately 20–24 feet in length. The extent of this rapid growth is very dependent on temperature, soil conditions and cultural practices.

VIII. Variability of Botanical Characteristics

Because of the variability of climate, temperature, soil conditions and cultural practices, the dimensions of the various components of a hop plant, including stems, cones, leaves, laterals and internodes vary tremendously from one year to the next, from one field to the next within the same year; and even from one plant to the next within the same field. This variation produces substantial overlapping of dimensions when comparing varieties and results in these dimensions having little use for comparing varieties.

IX. Propagation Methods

Asexual reproduction assures genetic stability and is used for increasing plant rootstock numbers to provide sufficient plants for commercial hop production. Sexual reproduction by this plant would result in genetic variability and therefore is undesirable other than for breeding purposes. The propagation methodology utilizes 1 to 2 inch vegetative cuttings, which are treated with a rooting hormone and planted in potting media in greenhouses. The treated cuttings are grown in greenhouses under rigorously controlled conditions, including without limitation control of temperature, humidity, light intensity, and day length conditions.

DETAILED DESCRIPTIVE INFORMATION

Following is a detailed description of the botanical and analytical chemical characteristics of the new variety. The information for the following botanical description was either collected or verified during the growing season of 1993 in the growing area west of Toppenish, Wash. These botanical characteristics, and to a lesser degree the analytical chemical characteristics, are dependent on cultural practices and climatic conditions and can vary with location and season:

1. Parentage: A hop plant originating from a controlled cross pollination between an unpatented Haas female hop No. 832-17 with unpatented Haas male hop No. 833-53M.
2. Locality where grown and observed: Toppenish, Washington
3. Dates of first and last harvest: Approximately August 28 and September 10 respectively in Toppenish, Wash.
4. Plant: Green, vigorous, climbing vine.
   *Plant shape.*—Capitate.
   *Leaf arrangement.*—Opposite.
   *Number of leaf lobes.*—3 or 5 (mostly 5).
   *Leaf margin.*—Dentate.
   *Stripe.*—Green.
   *Stipule direction.*—Down.
   *Lateral.*—37 inches average.
   *Internode length.*—11 inches average.
5. Cone characteristics:
   *Bract tip shape.*—Attenuate to Acute.
   *Bract tip position.*—Loosely appressed.
   *Bracteole tip shape.*—Narrowly rounded.
   *Compactness.*—Medium tight.
   *Shape.*—Ovoid.
   *Cone length.*—1 and ½ inches average.
   *Cone tip shape.*—Pointed.
   *Strig.*—Thick.
   *Yield per acre.*—1800 to 2200 pounds/acre.
   *Maturity.*—Medium.
6. Color characteristics: Fall color characteristics are unknown because the leaves are totally removed and destroyed during the harvesting procedure. However, using the Pantone Color Specifier 747XR from the Pantone Library of Color No. 1, the following pre-harvest color characteristics for H87311-3 have been determined:
   *Leaf upper surface.*—350U.
   *Leaf lower surface.*—364U.
   *Bine background.*—383U.
   *Bine stripe.*—384U.
   *Cone.*—383U.
   *Sidearm stem.*—377U.
7. Analytical data of cones:

| | |
|---|---|
| % Alpha Acids (Bale)* | 16.5 to 18.5 (ASBC spectrophotometric method) |
| % Beta Acids (Bale)* | 5.8 to 6.8 (ASBC spectrophotometric method) |
| Alpha/Beta Ratio* | Average 2.8 |
| Cohumulone (% of Alpha Acids) | Average 50.0 |
| Colupulone (% of Beta Acids) | Average 75.0 |
| Storage Characteristics* | 30.0% transformation after 6 months at 22° C. (Based on USDA Hop Storage Index) |
| Total Oils (mls/100 g)* | Average 3.4 |
| Humulene (% of Total Oils) | Average 15.0 |
| Caryophyllene (% of Total Oils) | Average 8.3 |
| Humulene/Caryophyllene Ratio | Average 1.8 |
| Farnesene (% of Total Oils) | 0.0 (zero) |
| Myrcene (% of Total Oils) | Average 50.0 |
| Lupulin (% of Total Cone Weight)** | Average 34 |

*Analaytical data determined on hops with approximately 8% cone moisture.
**Analytical data determined on hops with approximately 8% cone moisture.

8. Analytical data of lupulin:
   *% Alpha acids.*—Average. 52.0.
   *% Beta acids.*—Average 19.0.
9. Disease resistance: The variety H87311-3 is moderately susceptible to downy mildew. It should be noted that there is no known resistance to downy mildew in any variety of hop. H87311-3 is tolerant to strains of verticillium wilt found in the state of Washington growing area. It is also tolerant to the viruses found in the USA growing areas as well as to the major soil-borne pests including Phytophera root rot.
10. Regional adaptation: The H87311-3 variety is principally adapted to the drier growing region of the United States, specifically including the Toppenish, Wash. area, and to other relatively dry growing regions with similar climatic and daylight/daylength conditions.
11. Ploidy: The genetic make up of H87311-3 is 832-17 (Galena×63015M)×833-53M (21055×63015M). Both parents are diploid thus making H87311-3 a diploid plant. Because it is diploid, this plant is capable of reproduction either by asexual or sexual reproduction.
12. Life expectancy: Lift expectancy of this variety is now known, but presumed to be theoretically indefinite, similar to other varieties of the same species.
13. Use: Flavoring for beers, stouts, and ales.
14. Virus and propagation status: H87311-3 rootstock has been virus-tested and is virus free. Propagatable plant material exists.

Distinguishing Characteristics

There are a few characteristics which are less variable and can be useful in comparing varieties. These include the direction of the stipules, color of the bine edges (stripes), the shapes and colors of the cones, and the analytical data of the cones. The following observations were taken in the Toppenish growing area during the 1993 season.

The lateral length and growth habit of the laterals is very similar to the commercial hop variety, Galena. However, the following are characteristics which distinguish H87311-3 from Galena.

In the spring, H87311-3 has a more abundant shoot growth compared with Galena.

At bloom time in late June, H87311-3 has a tendency to develop some male flowers along with the female flowers, clearly distinguishing it from Galena as Galena does not have this tendency. This is more apparent some years than others.

During development, the bract tips of H87311-3 are lighter green and more appressed than those of Galena which are darker green and more recurved. This difference makes the cones H87311-3 appear lighter in color with smoother edges than Galena cones which have more of a striped, rough edged appearance. The bine stripe color, green, is similar in H87311-3 and Galena. H87311-3's deflexed stipule is also similar to Galena.

Harvest dates of H87311-3 are considered to be medium which is approximately the same time frame as the commercial variety Galena. The cones of this variety are fairly difficult to pick off of the vine. Drying times are longer than the variety Galena because of the heavier, denser cone.

Comparison of H87311-3 and Galena regarding analytical data shows H87311-3 with a much higher alpha acids content and lower beta acids content than Galena. This results in a much higher alpha beta ratio in H87311-3.

I claim:

1. A new variety of hop plant substantially as herein shown and described characterized particularly as to novelty by its cones' unusually high percentage of alpha acids when compared to its grandparent variety Galena (unpatented).

* * * * *

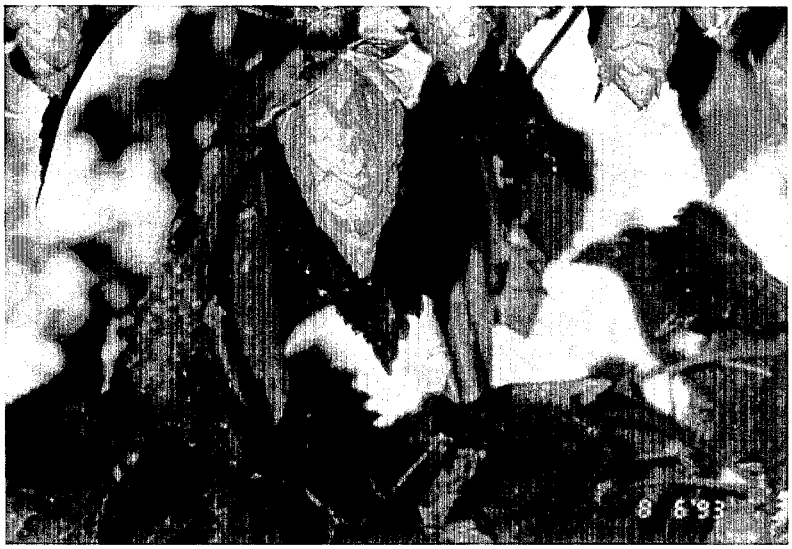
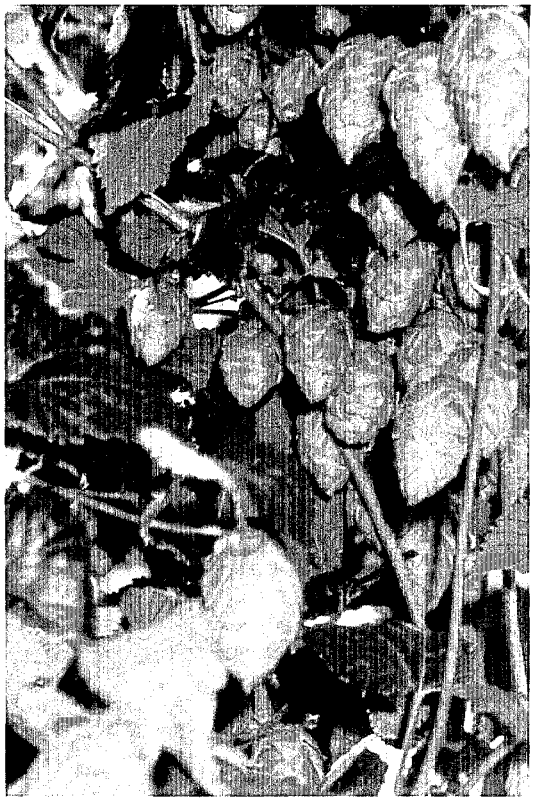

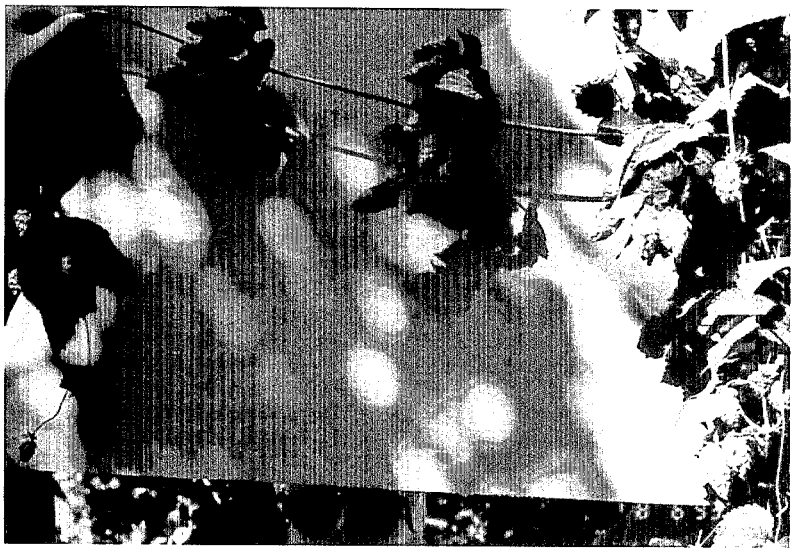
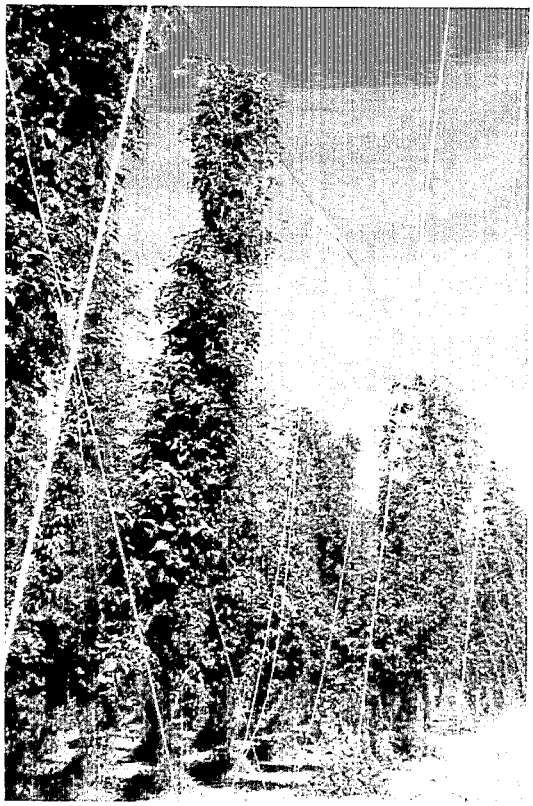

UNITED STATES PATENT AND TRADEMARK OFFICE

CERTIFICATE OF CORRECTION

PATENT NO. : Plant 8,812

DATED : June 28, 1994

INVENTOR(S) : Gene Probasco

It is certified that error appears in the above-indentified patent and that said Letters Patent is hereby corrected as shown below:

Column 8, line 62, change "lift" to --life--
Column 8, line 63, change "now" to --not--

Signed and Sealed this

Eighteenth Day of October, 1994

*Attest:*

Bruce Lehman

BRUCE LEHMAN

*Attesting Officer*

*Commissioner of Patents and Trademarks*